United States Patent
Krishnan et al.

(10) Patent No.: US 9,664,656 B2
(45) Date of Patent: May 30, 2017

(54) REAL-TIME GAS MONITORING METHOD AND SYSTEM

(75) Inventors: Narayan Krishnan, Brampton (CA); Santanam Sridhar, Brampton (CA)

(73) Assignee: Ruks Engineering Ltd., Brampton (CA)

( * ) Notice: Subject to any disclaimer, the term of this patent is extended or adjusted under 35 U.S.C. 154(b) by 413 days.

(21) Appl. No.: 14/232,432

(22) PCT Filed: Jul. 11, 2012

(86) PCT No.: PCT/CA2012/050475
§ 371 (c)(1),
(2), (4) Date: Jan. 13, 2014

(87) PCT Pub. No.: WO2013/006974
PCT Pub. Date: Jan. 17, 2013

(65) Prior Publication Data
US 2014/0156090 A1   Jun. 5, 2014

Related U.S. Application Data

(60) Provisional application No. 61/507,001, filed on Jul. 12, 2011.

(51) Int. Cl.
G05D 7/00 (2006.01)
G01N 33/00 (2006.01)
(Continued)

(52) U.S. Cl.
CPC ..... *G01N 33/0004* (2013.01); *G01N 33/0039* (2013.01); *G05D 7/0617* (2013.01);
(Continued)

(58) Field of Classification Search
USPC .................................................. 700/281–286
(Continued)

(56) References Cited

U.S. PATENT DOCUMENTS 3,875,380 A * 4/1975 Rankin ..................... F02C 9/40
                                                        60/39.281
4,039,804 A * 8/1977 Reed ......................... F02C 9/32
                                                        60/646

(Continued)

FOREIGN PATENT DOCUMENTS

CA   2466307   5/2003
EP   0477577   4/1992
(Continued)

OTHER PUBLICATIONS

Yamamoto et al, "Integrated Subsea Production System: An Overview on Energy Distribution and Remote Control", IEEE, pp. 173-181, 2014.*

(Continued)

*Primary Examiner* — Anil Khatri
(74) *Attorney, Agent, or Firm* — McMillan LLP

(57) ABSTRACT

A method for monitoring the concentration of a gas in an enclosed space is provided. A gas is injected into the space, by a gas injection system. The concentration of the gas is measured using a gas sensor. The concentration is compared with predetermined limits, and the gas injection system is shut off if the concentration is above one of the predetermined limits. In addition, hardware, software, and signal control elements which perform the monitoring, are continuously monitored for faults, and if a fault is detected, the gas injection system is shut off.

25 Claims, 1 Drawing Sheet

(51) Int. Cl.
*G05D 7/06* (2006.01)
*A61L 2/10* (2006.01)
*A61L 2/20* (2006.01)
*A61L 2/28* (2006.01)
*A61L 9/015* (2006.01)

(52) U.S. Cl.
CPC ............... *A61L 2/10* (2013.01); *A61L 2/202* (2013.01); *A61L 2/28* (2013.01); *A61L 9/015* (2013.01)

(58) Field of Classification Search
IPC .................................................. G01N 33/0004
See application file for complete search history.

(56) References Cited

U.S. PATENT DOCUMENTS

| | | | | |
|---|---|---|---|---|
| 5,526,280 | A * | 6/1996 | Consadori | G01N 33/0063 340/632 |
| 6,941,193 | B2 * | 9/2005 | Frecska | G05B 15/02 236/49.3 |
| 6,980,091 | B2 * | 12/2005 | White, II | H04B 3/56 333/24 R |
| 7,194,891 | B2 * | 3/2007 | Tuller | B01D 53/9409 73/24.01 |
| 7,464,721 | B2 * | 12/2008 | Perry | G05B 23/0256 137/12 |
| 7,617,055 | B2 * | 11/2009 | Henry | G01F 1/74 702/100 |
| 7,873,441 | B2 * | 1/2011 | Synesiou | G06Q 10/00 340/870.01 |
| 8,100,746 | B2 * | 1/2012 | Heidel | F24F 7/06 454/356 |
| 8,219,249 | B2 * | 7/2012 | Harrod | F24F 11/0086 62/150 |
| 8,252,229 | B2 * | 8/2012 | Thomas | A61B 5/14532 250/453.11 |
| 9,154,001 | B2 * | 10/2015 | Dharwada | H02J 13/001 |
| 9,459,564 | B2 * | 10/2016 | Ohsugi | G03G 15/162 |

FOREIGN PATENT DOCUMENTS

| | | |
|---|---|---|
| GB | 2425171 | 10/2006 |
| JP | 2009058204 | 3/2009 |
| WO | 2005/031297 | 4/2005 |

OTHER PUBLICATIONS

Tesfaye et al, "Upgrades to the Alcator C-MOD Gas System", IEEE, pp. 1-4, 2013.*
Guida et al, "The new gas injection system for the LINAC4 accelerator at CERN", IEEE, pp. 1-5, 2013.*
Jiang et al, "Manifold Concept Design for ITER Gas Injection System", IEEE Transactions on Plasma Science, vol. 40, No. 3, pp. 788-792, 2012.*
Aguiam et al, "Feasibility Study of a Control System based on PLC and EPICS for the ESTHER Combustion Gas Injection", IEEE, pp. 22-26, 2015.*
Shukla et al, "A Robust Statistical Scheme to Monitor Transient Phenomenon in Sensor Networks", IEEE, pp. 3907-3914, 2007.*

* cited by examiner

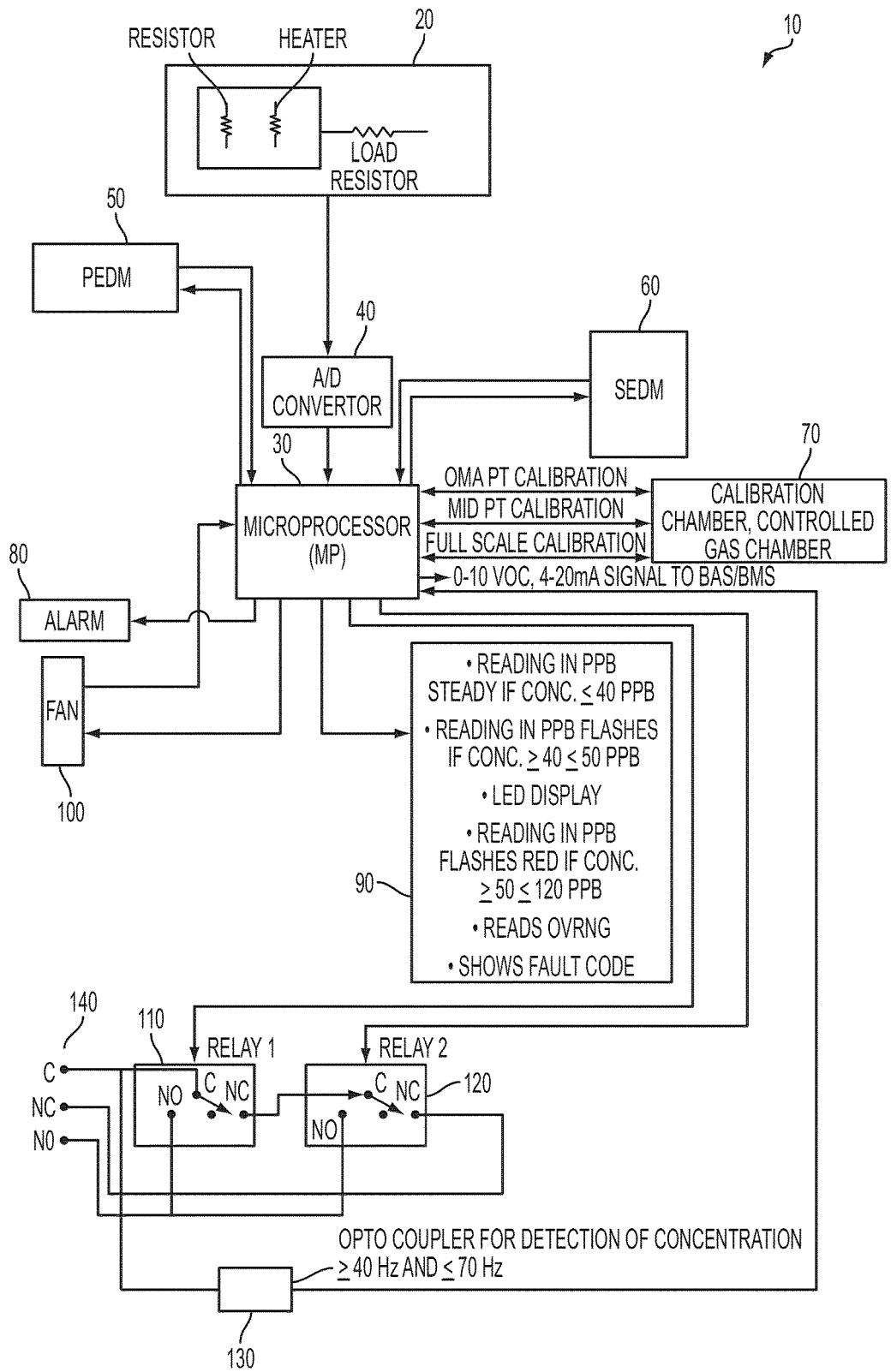

REAL-TIME GAS MONITORING METHOD AND SYSTEM

RELATED APPLICATIONS

This application claims priority to U.S. Provisional Application No. 61/507,001, the contents of which are herein explicitly incorporated by reference.

FIELD OF THE INVENTION

The invention relates to the field of gas monitoring systems, and more particularly to a gas monitoring method and system, for example an ozone monitoring method and system for continuous use in indoor air quality systems.

BACKGROUND OF THE INVENTION

Controlled ozone injection technology is commonly used in indoor air quality systems, and particularly in human occupied indoor space to suppress, or otherwise control odours. Recent research and development has shown that injecting ozone in a controlled fashion into indoor spaces is effective in controlling the air quality and level of unwanted odours in these spaces. For example, hotel, indoor spaces where smoking is still permissible, such as casinos, and in larger restaurants particularly within the confines of larger buildings such as shopping centres, airports and similar buildings, there is a strong need in the market to control the air quality and suppress undesirable odours that could otherwise make for an unpleasant visit. Controlled ozone injection technology is still in the relatively early stages of development and thus far, there are very limited standards related to the amount of ozone that may be safely injected into an indoor space. Accordingly, measurement of ozone in such indoor spaces thus far uses traditional sensing technologies capable of detecting ozone concentrations in the range of 1-100 parts per million. More recently, developments in the field have shown that more sophisticated sensing systems and methods may be necessary in order to detect and report upon ozone concentrations in the order of 10 parts per billion, and especially down to 2 parts per billion. Furthermore, these devices must operate in real-time and be essentially fail safe.

Furthermore, prior art ozone sensing methods and systems merely provide an indicator of ozone levels, without the ability of providing an active response. Prior art systems are also have a degree of downtime when a sensor fails, or other problems arise affecting the accuracy of the sensor readings. This can be particularly problematic in some indoor environments, for example particular manufacturing facilities that are sensitive to the amount of ozone in the air.

Accordingly, there is a need in the art for an improved indoor space gas, and particularly ozone, monitor for monitoring and/or detecting the levels of gas concentration in the indoor space.

SUMMARY OF THE INVENTION

According to one embodiment of the invention, there is provided a method for monitoring the concentration of a gas in an enclosed space into which the gas is being injected by a gas injection system. The method includes the steps of measuring a parameter indicative of gas concentration using a gas sensor, comparing the parameter with a predetermined limit value of the parameter using a microprocessor, and if the parameter is greater than the predetermined limit value then activating a shut-off of the gas injection system; and furthermore, continuously monitoring at least one of a hardware element, a software function and a control signal used to carry out the method to identify faults in at least one of the hardware element, the software function and the control signal; and if a fault is detected activating the shut-off of the gas injection system.

According to one aspect of the invention, the gas is ozone and the gas injection system is an ozone injection system.

According to another aspect of the invention, the parameter indicative of gas concentration is voltage.

According to another aspect of the invention, prior to the comparing step, converting the voltage into a digital value corresponding with the gas concentration such that the predetermined limit value is expressed in terms of a predetermined limit concentration.

According to another aspect of the invention, the method further includes calibrating the sensor prior to the measuring step.

According to another aspect of the invention, the calibrating step includes placing the gas sensor in a calibration zone, exposing the gas sensor to at least three known concentration levels of the gas, measuring a calibration parameter indicative of gas concentration at each of the at least three known concentration levels, and storing each the calibration parameter in a computer readable memory in communication with the microprocessor.

According to another aspect of the invention, the at least three known concentration levels comprise three concentration levels selected from the group comprising 0 PPB, a concentration level between 30-60 PPB and 100 PPB.

According to another aspect of the invention, the concentration level between 30-60 PPB comprises 40 PPB.

According to another aspect of the invention, the continuously monitoring step is carried out by a primary error detection module for identifying hardware faults and a secondary error detection module for identifying software and control faults.

According to another aspect of the invention, each of the primary and secondary error detection modules are integrated with the microprocessor.

According to another aspect of the invention, the method further includes the step of comparing the parameter with one or more predetermined state values of the parameter using the microprocessor, and providing an indication of a state of the gas based on the one or more predetermined state values on a display in communication with the processor.

According to another aspect of the invention, the predetermined state values include a predetermined safe state value and a predetermined warning state value.

According to another aspect of the invention, the predetermined safe state value is between 0-40 PPB and the predetermined warning state value is between 40-50 PPB.

According to another aspect of the invention, the method further includes circulating environment air to the proximity of the sensor using a fan positioned within a housing; wherein the housing contains the sensor and an air passage through which the fan circulates air.

According to another aspect of the invention, the hardware fault includes an identification of a fault in the fan; whereby the activating the shutoff occurs if the fault in the fan is detected.

According to another embodiment of the invention, there is disclosed a system for monitoring the concentration of a gas in an enclosed space into which the gas is being injected by a gas injection system. The system preferably includes a gas sensor for measuring a parameter indicative of gas concentration, a microprocessor for comparing the parameter with a predetermined limit value of the parameter, a shut-off means in communication with the microprocessor; wherein if the parameter is greater than the predetermined limit value then activating the shut-off means to shut-off the gas injection system, and an error detection means for continuously monitoring at least one of a hardware element, a software function and a control signal to identify faults in at least one of the hardware element, the software function and the control signal; whereby if a fault is detected activating the shut-off means to shut-off the gas injection system.

According to one aspect of this embodiment, the gas is ozone and the gas injection system is an ozone injection system.

According to another aspect of this embodiment, the parameter indicative of gas concentration is voltage.

According to another aspect of the invention, the system further includes an analogue/digital converter for converting the voltage into a digital value corresponding with the gas concentration such that the predetermined limit value is expressed in terms of a predetermined limit concentration.

According to another aspect of the invention, the system further includes calibrating means for calibrating the sensor.

According to another aspect of the invention, the calibrating means is adapted to receive the gas sensor in a calibration zone such that the gas sensor is exposed to at least three known concentration levels of the gas to determine a calibration parameter indicative of gas concentration at each of the at least three known concentration levels,; the system further comprising a computer readable memory in communication with the microprocessor for storing each the calibration parameter.

According to another aspect of the invention, the at least three known concentration levels comprise three concentration levels selected from the group comprising 0 PPB, a concentration level between 30-60 PPB and 100 PPB.

According to another aspect of the invention, the concentration level between 30-60 PPB comprises 40 PPB.

According to another aspect of the invention, the error detection means comprises a primary error detection module for identifying hardware faults and a secondary error detection module for identifying software and control faults.

According to another aspect of the invention, each of the primary and secondary error detection modules are integrated with the microprocessor.

According to another aspect of the invention, the microprocessor further compares the parameter with one or more predetermined state values of the parameter, and indicating means for providing an indication of a state of the gas based on the one or more predetermined state values on a display in communication with the processor.

According to another aspect of the invention, the predetermined state values include a predetermined safe state value and a predetermined warning state value.

According to another aspect of the invention, the predetermined safe state value is between 0-40 PPB and the predetermined warning state value is between 40-50 PPB.

According to another aspect of the invention, the system further includes a housing having an air passage providing a path for environment air to reach the sensor located within the housing, and a fan for circulating environment air to the proximity of the sensor.

According to another aspect of the invention, the hardware fault includes an identification of a fault in the fan; whereby the activating the shutoff occurs if the fault in the fan is detected.

BRIEF DESCRIPTION OF THE DRAWINGS

The FIGURE is a schematic view of the system according to the invention.

DETAILED DESCRIPTION

The invention provides for an improved method and system for monitoring ozone concentration levels in indoor spaces, and optionally for controlling ozone producing equipment in human occupied spaces when the ozone concentration exceeds a predetermined level. Generation of ozone in human occupied space is a common occurrence. For example, the use of office equipment that produce ozone as a byproduct such as photocopiers and printers is a common source of unintended, or otherwise uncontrolled source of ozone. Another example of the introduction into indoor spaces of ozone is the production of ozone by indoor air quality improvement devices such as electrostatic precipitators and ultra violet germicidal systems to disinfect room air and HVAC components. These are all examples of ozone being released into indoor spaces as a byproduct of other functions. As described earlier, it is also becoming common to inject ozone into indoor spaces using ozone generators by intended design, for example as is the case in some indoor air quality systems. It has recently been discovered that maximum permissible concentrations of ozone in human occupied indoor spaces, and particular when ozone is intentionally injected into these indoor spaces is in the order of 50 parts per billion (PPB). This is orders of magnitude lower than conventional ozone monitors are able to detect. Furthermore, as far as is known to the applicant, prior art ozone monitors have been unable to operate in real time by incorporating substantial fail safe elements that would shut down an ozone injection system in the event the ozone monitor determines that a higher than acceptable ozone concentration is present, or if a fault is found in the ozone monitor itself. This is particularly applicable in ozone injection applications where ozone is intentionally injected into a space for comfort. In these applications there is no concern as to a lack of ozone, but rather only to an excess of ozone. Accordingly, shutting down the ozone injecting system is acceptable for safety reasons, but injecting too much ozone into the space is unacceptable. The invention is not limited to ozone monitoring, and in some embodiments other gases may be monitored by using particular sensors adapted to measure the concentration of other gases. In still further embodiments, sensor elements may be readily interchanged in a manner that permits the monitoring unit to be customizable with respect to the gas being monitored by virtue of interchanging a sensor element in the device. An interchangeable sensor is considered to be another novel aspect of the invention, whereby a sensor and/or sensor module may be readily interchanged within the gas monitoring device to adapt the gas monitoring device for monitoring other gases without substantially altering the design or software of the device itself. While the description of the preferred embodiments that follow generally describe the invention with respect to ozone, it will be appreciated by a person skilled in the art that other gases may also be monitored, and the invention is not limited to particular gases.

Referring now to the FIGURE, there is shown a schematic of a general embodiment of a gas, and preferably an ozone, monitoring device according to the invention. The ozone monitoring device 10 preferably includes an ozone sensor 20 arranged to provide a signal indicative of ozone concentration to a microprocessor 30. The signal from the sensor 20 is typically an analogue signal that is converted to a digital signal by an analogue-digital converter 40 prior to being communicated to the microprocessor 30. This type of conversion, and the interaction between analogue sensors and digital signal processing equipment (such as a microprocessor) are known in the art, and not described further herein. The microprocessor 30 has integrated therewith, or is otherwise in communication with a number of modules or functional elements that provide for the operation of the monitoring device 10. Following immediately below is a general description of the functions of each of these elements, with a detailed description following thereafter.

An error detection module is preferably integrated with, but may also be an additional component in communication with, the microprocessor 30 and performs a self-diagnosis of all functions occurring in the device on a predetermined timed schedule. A primary error detection module (PEDM) 50 is provided and is adapted to deliver a signal to the microprocessor to activate a shut-off relay if any faults are detected. The microprocessor 30 may then display a fault code associated with a particular detected failure on a display 90 or other user interface. In a similar manner, a secondary error detection module (SEDM) 60 is provided, preferably integrated with the microprocessor 30 that checks for the accuracy of software functions, control signals and/or data being communicated throughout the system. That is, SEDM 60 checks for the accuracy of binary digits with critical functions. Based on the check at the SEDM 60, the microprocessor may activate a shut-off relay if software-side faults are found indicating a possible corruption of software or data being transmitted, for example. Accordingly, when considered in combination, the PEDM 50 and the SEDM 60 provide for complete and near fail-safe operation of the device 10 by providing an oversight in the system as a whole for faults related to hardware components, functions being delivered, software used on the system and data being transmitted throughout the system.

The microprocessor 30 itself is generally adapted to provide an output to the display 90 indicative of the concentration of ozone in the environment being monitored. For example, an indication may be provided that the concentration is below 40 PPB, and therefore within acceptable limits, another indication if the concentration is between 40 PPB and 50 PPB indicative of a warning zone, and another indication if the concentration is greater than 50 PPB and less than 120 PPB and therefore indicative of being outside of acceptable ozone limits.

Ultimately, the microprocessor 30 is preferably adapted to provide an emergency stop signal to an air quality correctional device (not shown), such as an ozone injection device as described above. Thus, a first relay 110 is preferably connected to the microprocessor 30 to provide a stop signal, or otherwise trigger a stop signal to an non-system component 140, when the PEDM 50 indicates a fault through its diagnosis of the operating functions of the monitoring device 10. A second relay 120 is also preferably connected to the microprocessor 30 to provide a stop signal, or to otherwise trigger a stop signal to the non-system component 140, when the SEDM 60 identifies a corruption in software, data or other information transmitted throughout the device. The invention is not restricted to the relays 110 and 120 as described above, and one skilled in the art will appreciate that any means for triggering an action, particularly a cessation action to non-system component 140 in a building automation, air quality or HVAC system is contemplated by the invention. These means are generally known in the art and are therefore not described in further detail. The term non-system component is used to identify any component that does not form part of the ozone monitoring device of the invention, and is not intended to be limited in any other manner.

An internal fan 100 is preferably provided within the monitoring device 10 to circulate environment air through the monitoring device 10 ensuring a constant air flow through the monitoring device to the sensor 20. That is, one or more air flow channels are provided within the monitoring device 10 that permits that sensor to be in contact with air from the environment. The fan 100 ensures circulation of air through the air flow channels.

Having thus described the general operation of the device according to the invention, below follows a detailed description of each of the components that when used in combination, and the manner described herein forms the invention.

The Sensor

Sensor 20 is preferably provided in a removable and interchangeable module 22. The removable and interchangeable module 22 is adapted to be plugged into the device 10, and removed therefrom thus permitting the gas monitoring device 10 to be readily adapted for monitoring different types of gases, without having to assemble or design an altogether new monitoring device 10. For example, the sensor 20 may be provided in a module that uses "plug and play" type electrical connectors to integrate with the rest of the monitoring device 10. The module 22 is preferably insertable into the monitoring device 10 at a location that permits the sensor to be in contact with the air channels though which the fan 100 circulates air within the monitoring device 10.

While various types of sensors may be used with the invention, in the preferred embodiment, the sensor 30 includes a semi-conductor based sensing element generally including a thinly formed substrate 32 of alumina with gold electrodes 34. This type of sensor is generally known in the art and works on metal oxidization principles to output a change in voltage in relation to a change in concentration of the gas being monitored. A film heater 36 is provided within the sensing element to maintain a constant temperature on the sensing element. Preferably, the sensing element is rated for continuous operation. The output signal from the sensor is preferably normalized and conditioned to deliver an analogue signal such as 0 to 10 VDC and 4 to 20 mA.

The Primary Error Detection Module (PEDM)

Many factors cause improper operation or failure of monitors and sensing elements. For example, all sensing elements drift and age over time. Drift or ageing of sensor elements results in inaccurate readings. The PEDM of the invention is adapted to continually detect deviations from an original value, and if this is beyond acceptable value, it activates a relay, which in turn deactivates the ozone producing device. Finally, the PEDM preferably generates and arranges for the display of an identifiable fault code, particular to each failure mode to inform the user of the reason for deactivation. Accordingly, any fault in the sensor results in the termination of ozone being injected into the environment.

Another possible cause of improper operation is due to the lack of adequate care and handling of the device in general that may cause damage to the microprocessor or related components resulting in reduced accuracy or impaired performance. In one embodiment, the microprocessor 30 is a trace enabled microprocessor that outputs traces including a history of the instructions executed by the microprocessor, context switches between various tasks carried out by the monitoring device and addresses and values written to or read from specific parts of the memory. As is generally known in the art, trace data can be collected in an entirely non-intrusive fashion, permitting the PEDM to oversee the operations of the monitoring device with no impact on the operation of the device itself. As the trace data is collected, the PEDM compares the trace data to baseline values that are preloaded for specific device functions. If a device value deviates from the baseline value by a predetermined amount, the PEDM registers an error. Accordingly, the PEDM is adapted to continually detect faults in traces of the microprocessor board, and deactivates the ozone producing device in response to a fault being detected. Furthermore, a fault code is preferably presented either on the PEDM or on the display 90. One example or a fault event that the PEDM would register is if the microprocessor provides an indication that the fan 100 is operating in a manner that deviates from its normal operation. As the fan 100 is adapted to provide constant and consistent air flow through the internal air chambers, an even slightly malfunctioning fan 100 could result in inaccurate monitoring of the ozone being monitored. Accordingly, if the PEDM identifies a fault in the fan, a signal is sent to the microprocessor 30 that ceases operation of the ozone injecting equipment.

Other examples of a fault event that may be detected by the PEDM include detecting failures in the sensor itself, for example a loss of calibration that has not been restored. As the sensitivity of the calibration is important to the proper measurement of ozone present in the environment, monitoring the calibration becomes equally as important. Aspects of the invention also relate to how this calibration is performed, and will be described further below. In any event, the results of the calibration method may be stored and checked back with a calibration constant that is stored to determine whether a loss of calibration has occurred.

The PEDM may be implemented as a software module stored in non-volatile memory associated with the microprocessor.

Other hardware failures or errors will be detected by methods readily implemented by a person skilled in the art in view of this description.

The Secondary Error Detection Module (SEDM)

The SEDM provides fault detection for software, data and control signals being communicated throughout the device. The advantage of separating fault detection for software/data problems from fault detection for hardware problems is that the PEDM can detect faults in the SEDM, and vice versa. It should be noted that the terms "primary" and "secondary" when used to describe the error detection modules refer only to hardware and software/data error detection. The terms are not meant to connote a preference, or hierarchy of error detection. It is readily contemplated that the terms primary and secondary may be interchanged as descriptors for the two error detection nodules.

In a preferred embodiment, the SEDM preferably includes self-diagnostic circuitry and stores a combination of bits for all outputs of data/control signals in the ozone monitor and relates this combination of bits to the specific task such bits are expected to perform. Each function is stored in the microprocessor. Any type of self-diagnostic circuitry may be used, and some are known in various arts. However, the application of self-diagnostic circuitry to an ozone/gas monitoring device is believed to be novel, and is particularly useful when provided in combination with the other elements of the invention as herein described. The self-diagnostic circuitry checks these stored bits at predetermined timed intervals, for example every 2 seconds, to detect if there is any corruption in these stored bits, which would indicate a corruption in stored data, software or control signals. If a software malfunction would ever occur resulting in flipping of the digits of the bits (that is, indicative of data corruption), a fault is detected and reported as a fault. This occurs at each interval at which the self-diagnostic circuitry checks for errors. Not all software faults are considered critical, but all are preferably reported. The critical functions are defined and stored in the microprocessor, as the non-critical ones are also defined and stored. The critical sub-functions are defined as those that are, for example, relevant to determining the concentration of the tracked gas, delivery of analog signals, and activation of the relay contact to shut off the supply of ozone. Non critical functions are defined as those that add user benefit features, cosmetic and aesthetic features, and other optional features of the system. If an error is noted in bits that relate to critical functions, the microprocessor understands this as a critical function and deactivates the relay to cause shutdown of the ozone generating device and/or activation of a gas concentration diluting device such as a fan. If an error is detected relating to non-critical functions, it is conceivable that no specific action is require and the device can continue to operate as usual.

Calibration

Another aspect of the invention relates to the calibration of the ozone sensor, that facilitates the capabilities provided by the invention to monitor ozone concentrations to levels heretofore unknown in the art. In particular, the calibration method according to the invention uses a predetermined number of calibration points, preferably three calibration points, set at 0, 50 and 100 PPB, for example. In the preferred embodiment, the calibration points are set at 0, 40 and 100 PPB to accommodate the non-linearity of the ozone sensor. That is, a calibration zone is arranged having known levels of ozone concentration. The ozone sensor is positioned within the calibration zone and the depending on the ozone level in the calibration zone, a different resistance is applied to a voltage passing through the sensor. Accordingly, fine calibrations are obtained from this method, the results of which can be stored as the known in the art, and further used to detect a loss of calibration as described above. In other embodiments, more than three calibration points may be used, and the invention should be construed as being limited to three calibration points only, although it has been found that the use of three calibration points yields results that are particularly advantageous for implementing the invention.

As is known, it is not possible to procure ozone cylinders of known concentration. In order to obtain the calibration as described above in the calibration zone, it is necessary to produce ozone in situ. The half life of ozone is relatively short and thus producing ozone at concentrations of between 0 PPB, 50 PPB and 100 PPB for a period of time (typically 2 to 5 minutes) sufficient to complete the calibration can be a formidable task. Applicant has discovered that by using two or more ultra violet lamps, each provided with a slideable metallic shield that is manipulated to vary the surface area of exposure, it is possible to produce benchmark concentrations of ozone. Once the ozone concentration within the calibration zone is known and held stable, at least for a period of time, the ozone sensor used with the device of the invention can be placed within the calibration zone and the readings calibrated. This process is repeated for each level of ozone concentration, and in the preferred example, at 0, 40 and 100 PPB.

Use of the Device

Potential benefits of this invention include ensuring safety and compliance to regulatory mandates and trade bodies for occupants of rooms where ozone emitting office equipment is used, warning of higher than permissible ozone in confined welding shops, indoor air quality improvement devices such as electrostatic precipitator, electronic air filters, UV air disinfection, ozone generators, are proven to improve indoor air quality and eliminate smoke and odor, at reasonable costs.

Monitoring outdoor or ambient ozone with this invention will enhance the performance of Demand Load Ventilation, as a means of regulating outdoor air into air conditioned or ventilated premises, resulting in improved indoor air quality and reduced operating costs of HVAC systems.

During normal operation, in response to a specific concentrations in the environment, the sensor references the detected concentration to that of the stored calibration, and using software stored on the device, presents the actual concentration. An alarm threshold level may be set based on a predetermined gas concentration. Activation of the relay contact, to disable segments of the building air quality or HVAC system is also achieved through a predetermined gas concentration.

To ensure extensive reliability, a self diagnosis in short time intervals, preferably every 2 seconds is performed. All values of proper functioning for each of the hardware, software, control and data components are saved in the memory in communication with the microprocessor. While the PEDM and the SEDM perform the self diagnostics, one of the two detects the present value for each function and compares it with the stored value of the corresponding function. A built in tolerance may be permitted. If the sensed parameter is beyond the stored value including the tolerance, this is interpreted as a malfunction. Preferably, these incidences are converted to digital codes by the microprocessor and reported on a display as a malfunction, using a specific code number for each type of failure. This task is also performed by sub-functions. As will be appreciated by one skilled in the art, any number of faults may be defined to ensure continuous monitoring of ozone going into an environment.

Due to the storage of calibration results using the three point calibration discussed above, gas, and particularly ozone can be accurately measured down to 2 PPB (Parts Per Billion) For further enhancement and greater accuracy, multiple point calibration other than three can also be performed. As will now be appreciated by a person skilled in the art, when taken to an extreme, an infinite number of calibration points could theoretically be stored in the memory, allowing for an extremely high level of accuracy. Depending on the extent of accuracy required in a particular application, the number of calibration points may be selected and performed. This flexibility allows the device to be suitable for use in wide range of applications, as each application may require a different level of accuracy.

Various modifications and alterations may be possible to the various embodiments as herein described that would be appreciated by a person skilled in the art having regard to this description. Accordingly, the scope of the claims should not be limited by the preferred embodiments set forth in the examples, but should be given the broadest interpretation consistent with the description as a whole.

We claim:

1. A method for monitoring a concentration of a gas in an enclosed space, comprising:
    injecting said gas into said enclosed system using a gas injection system;
    measuring a parameter indicative of said gas concentration using a gas sensor;
    comparing said parameter with a predetermined limit value of said parameter using a microprocessor, and if said parameter is greater than said predetermined limit value then activating a shut-off of the gas injection system;
    continuously monitoring one of a hardware element, a software function and a control signal used to carry out the method to identify at least one fault in at least one of said hardware element, said software function and said control signal; and
    if a fault is detected activating said shut-off of the gas injection system;
    wherein said continuously monitoring step is carried out by one of a primary error detection module for identifying hardware faults and a secondary error detection module for identifying software and control faults;
    wherein each of said primary and secondary error detection modules are integrated with said microprocessor.

2. A method according to claim 1, wherein said gas is ozone and said gas injection system is an ozone injection system.

3. A method according to claim 1, further comprising, prior to said comparing step, converting said parameter into a digital value corresponding with said gas concentration such that said predetermined limit value is expressed in terms of a predetermined limit concentration.

4. A method according to claim 3, further comprising calibrating said sensor prior to said measuring step.

5. A method according to claim 4, wherein said calibrating step comprises placing said gas sensor in a calibration zone, exposing said gas sensor to at least three known concentration levels of said gas, measuring a calibration parameter indicative of gas concentration at each of said at least three known concentration levels, and storing each said calibration parameter in a computer readable memory in communication with said microprocessor.

6. A method according to claim 5, wherein said at least three known concentration levels comprise three concentration levels selected from the group comprising 0Parts Per Billion (PPB), a concentration level between 30-60 PPB and 100 PPB.

7. A method according to claim 1, wherein said continuously monitoring step is carried out by a primary error detection module for identifying hardware faults and a secondary error detection module for identifying software and control faults.

8. A method according to claim 1, further comprising the step of comparing said parameter with one or more predetermined state values of said parameter using said microprocessor, and providing an indication of a state of said gas based on said one or more predetermined state values on a display in communication with said processor.

9. A method according to claim 8, wherein said predetermined state values include a predetermined safe state value and a predetermined warning state value.

10. A method according to claim 9, wherein said predetermined safe state value is between 0-40 PPB and said predetermined warning state value is between 40-50 PPB.

11. A method according to claim 1, further comprising circulating environment air to the proximity of said sensor using a fan positioned within a housing; wherein said housing contains said sensor and an air passage through which said fan circulates air.

12. A method according to claim 11, wherein said hardware fault includes an identification of a fault in said fan; whereby said activating said shutoff occurs if said fault in said fan is detected.

13. A system for monitoring a concentration of a gas in an enclosed space, comprising:
   a gas injection system for injecting said gas into said enclosed space;
      a gas sensor for measuring a parameter indicative of said gas concentration;
   a microprocessor for comparing said parameter with a predetermined limit value of said parameter;
   a shut-off means in communication with said microprocessor; wherein if said parameter is greater than said predetermined limit value then activating said shut-off means to shut-off the gas injection system; and
   an error detection means for continuously monitoring one of a hardware element, a software function and a control signal to identify faults in one of said hardware element, said software function and said control signal; whereby if a fault is detected activating said shut-off means to shut-off the gas injection system;
   wherein said error detection means comprises one of a primary error detection module for identifying hardware faults and a secondary error detection module for identifying software and control faults;
   wherein each of said primary and secondary error detection modules are integrated with said microprocessor.

14. A system according to claim 13, wherein said gas is ozone and said gas injection system is an ozone injection system.

15. A system according to claim 13, further comprising an analogue/digital converter for converting said parameter into a digital value corresponding with said gas concentration such that said predetermined limit value is expressed in terms of a predetermined limit concentration.

16. A system according to claim 15, further comprising calibrating means for calibrating said sensor.

17. A system according to claim 16, wherein said calibrating means is adapted to receive said gas sensor in a calibration zone such that said gas sensor is exposed to at least three known concentration levels of said gas to determine a calibration parameter indicative of gas concentration at each of said at least three known concentration levels the system further comprising a computer readable memory in communication with said microprocessor for storing each said calibration parameter.

18. A system according to claim 17, wherein said at least three known concentration levels comprise three concentration levels selected from the group comprising 0 PPB, a concentration level between 30-60 PPB and 100 PPB.

19. A system according to claim 13, wherein said error detection means comprises a primary error detection module for identifying hardware faults and a secondary error detection module for identifying software and control faults.

20. A system according to claim 13, wherein said microprocessor further compares said parameter with one or more predetermined state values of said parameter, and indicating means for providing an indication of a state of said gas based on said one or more predetermined state values on a display in communication with said processor.

21. A system according to claim 20, wherein said predetermined state values include a predetermined safe state value and a predetermined warning state value.

22. A system according to claim 21, wherein said predetermined safe state value is between 0-40 PPB and said predetermined warning state value is between 40-50 PPB.

23. A system according to claim 13, further comprising a housing having an air passage providing a path for environment air to reach said sensor located within said housing, and a fan for circulating environment air to the proximity of said sensor.

24. A system according to claim 13, wherein said hardware fault includes an identification of a fault in said fan; whereby said activating said shutoff occurs if said fault in said fan is detected.

25. A system according to claim 13, wherein said gas sensor is interchangeable, such that the system can readily be adapted for monitoring different types of gases.

* * * * *